United States Patent
Schmitt et al.

(10) Patent No.: US 11,259,909 B2
(45) Date of Patent: *Mar. 1, 2022

(54) DEVICE FOR COLLECTING ANIMAL SEMEN

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 287 days.

This patent is subject to a terminal disclaimer.

(21) Appl. No.: 16/419,441

(22) Filed: May 22, 2019

(65) Prior Publication Data

US 2019/0358011 A1 Nov. 28, 2019

(30) Foreign Application Priority Data

May 24, 2018 (FR) ...................................... 1854411

(51) Int. Cl.
*A61D 19/02* (2006.01)
*A61B 10/00* (2006.01)

(52) U.S. Cl.
CPC ........ *A61D 19/021* (2013.01); *A61B 10/0058* (2013.01); *A61D 19/022* (2013.01)

(58) Field of Classification Search
CPC ................ A61D 19/021; A61D 19/022; A61B 10/0058; A61B 10/0045; B07B 1/469; B01D 29/00–01; B01D 23/06; B01D 23/28; B01D 46/2422; B01D 46/2425; B01D 46/2429; B01D 2201/02
See application file for complete search history.

(56) References Cited

U.S. PATENT DOCUMENTS

| 5,590,581 A | 1/1997 | Strub et al. |
| 5,961,503 A | 10/1999 | Simmet et al. |
| 2009/0137974 A1* | 5/2009 | Yvoz .................... A61D 19/021 604/349 |
| 2015/0150666 A1 | 6/2015 | Muller |

FOREIGN PATENT DOCUMENTS

| CN | 106479869 A | 3/2017 |
| FR | 2 614 899 | 11/1988 |
| WO | 2006131781 A1 | 12/2006 |

* cited by examiner

*Primary Examiner* — Kaylee R Wilson

(74) *Attorney, Agent, or Firm* — Browdy and Neimark, P.L.L.C.

(57) ABSTRACT

The device (1) comprises an inlet element (28) comprising an interface (40) for connecting to an artificial vagina and delimiting an inlet opening (14), a filter delimiting with the inlet element (28) an inlet chamber (41) on the side of the filter turned towards the opening (14) and a collection bag (4) extending between a closed end (8) and an open end (7) in which said inlet element is engaged; said bag and said filter delimiting a collection chamber (42) on the side of the filter turned towards the end (8); by means of which the semen entering through the opening (14) passes through the filter and comes to the collection chamber (42); the filter being a perforated wall (30) having a tubular portion (22) and a bottom portion (15) closing said tubular portion, and having a surface density of orifices (24) that is greater on said bottom portion than on said tubular portion.

14 Claims, 3 Drawing Sheets

DEVICE FOR COLLECTING ANIMAL SEMEN

FIELD OF THE INVENTION

The present invention relates to the general field of the collection of animal semen, in particular pig semen, and more precisely to the devices for collecting this semen.

TECHNICAL BACKGROUND

International application WO 2006/131781 discloses a device for the collection of animal semen, comprising a rigid frame to which a non-woven fabric filtration pouch and a collection bag are fixed, the filtration pouch being positioned inside the collection bag. The rigid frame comprises an adaptation part for assembling the device with an artificial vagina and an armature which maintains the shape of the filtration pouch over its entire height. The adaptation part has a geometry adapted to the outlet of the artificial vagina and delimits a passage for the flow of the animal semen from the artificial vagina to the filtration pouch. The collection bag has a pre-cutout line in order to make it possible to separate the part of the bag intended to collect the semen from the part of the bag fixed to the frame. The animal semen flowing from the artificial vagina is filtered by the pouch then collected in the bag. The filtration carried out by the pouch makes it possible to remove from the semen an undesirable substance forming a sort of gel, called "tapioca". Once collected in the collection bag, the animal semen is analyzed in a specific room, often called laboratory, then it is diluted before being preserved in individual packets.

OBJECT OF THE INVENTION

The invention aims to provide a device for the collection of animal semen that is more effective that the known devices, while remaining simple, convenient and economical.

To this end, the invention proposes a device for the collection of animal semen, comprising:
  an inlet element comprising a mechanical interface for connection to an artificial vagina and delimiting an inlet opening in the collection device;
  a filter associated with the inlet element and delimiting with the inlet element an inlet chamber extending on the side of a first face of the filter turned towards the inlet opening; and
  a collection bag extending between a closed distal end zone and a proximal end zone having an opening in which said inlet element is engaged; with said bag which is fixed to said inlet element; and with said bag and said filter which delimit a collection chamber extending on the side of the second face of the filter turned towards the closed distal end zone of the bag;
  by means of which the semen entering the device via the inlet opening passes through the filter and is collected in the collection chamber;
  characterized in that the filter is formed by a perforated wall having a tubular portion extending axially between a first end turned towards said proximal end zone of said bag and a second end turned towards said closed distal end zone of said bag and a bottom portion extending transversally to said tubular portion and closing the latter at its second end; said perforated wall is perforated by a plurality of orifices distributed over said perforated wall being arranged on said tubular portion according to a first predetermined pattern and on said bottom portion according to a second predetermined pattern, said first predetermined pattern and second predetermined pattern providing a surface density of orifices that is greater on said bottom portion than on said tubular portion.

With such a density of orifices that is greater in the bottom than in the side wall, the filter that comprises the collection device according to the invention is particularly well adapted to the semen filtration requirements during the collection thereof: given that the semen first essentially comes into contact with the bottom of the filter, it is this bottom which begins the filtration of the semen and first collects the "tapioca" that the filter must retain.

The high density of orifices on the bottom makes it possible for the liquid part of the semen to flow through the bottom under optimum conditions.

When the quantity of "tapioca" collected by the bottom starts to become significant, it becomes more difficult for the semen to flow through the bottom orifices, the level of semen in the filter increases and the orifices in the side wall make it possible for the liquid part of the semen to continue to flow through the filter under good conditions.

The lower surface density of orifices in the side wall makes it possible to maintain an excellent balance between the reduction in the orifices available in the bottom due to their being covered by the "tapioca" and the increase in the level of semen in the filter which brings it into contact with additional orifices forming part of the side wall.

The semen-filtering performance obtained with the filter according to the invention is particularly high, in particular with respect to the proportion of the liquid part of the semen passing through the filter and thus collected in the bag and also in the flow time of the semen through the filter.

According to simple, convenient and economical characteristics of the collection device according to the invention:
  said perforated wall forms a single piece with said inlet element;
  said tubular portion has a circular cross-section;
  said tubular portion has a ribbed outer face;
  said ribbed outer face has straight ribs orientated longitudinally like the axial orientation of the tubular portion;
  said ribs are distributed around the tubular portion according to a predetermined angular pitch;
  said orifices have a predetermined minimum diameter comprised between 0.5 mm and 1.5 mm, said surface density of orifices being comprised between 3 and 16 orifices per $cm^2$;
  said first predetermined pattern provides a surface density of orifices on the tubular portion comprised between 3 and 7 orifices per $cm^2$;
  said second predetermined pattern provides a surface density of orifices on the bottom portion comprised between 10 and 16 orifices per $cm^2$;
  according to at least one of said first predetermined pattern and second predetermined pattern, said orifices are arranged in a grid of rectangles;
  according to at least one of said first predetermined pattern and second predetermined pattern, said orifices are arranged in a quincunx;
  each of said orifices is delimited by a funnel-shaped surface increasing in diameter towards the second face of the filter;
  said inlet element and said perforated wall form part of a piece made from injection-moulded thermoplastic material;

the material from which said perforated wall is made comprises a polyolefin-type polymer having a surface tension less than 30 dynes; and/or said device comprises a protection bag which covers said collection bag and which is fixed to said inlet element.

BRIEF DESCRIPTION OF THE DRAWINGS

The disclosure of the invention will now be continued with the detailed description of embodiments, given below for the purposes of illustration and non-limitatively, with reference to the attached drawings. Therein.

DETAILED DESCRIPTION OF EMBODIMENT EXAMPLES

The semen collection device 1 illustrated in FIGS. 1 to 4 comprises a collection bag 4 (only shown in FIGS. 1 and 2) and a filtration cup 5.

The collection device 1 is here configured to be connected to an artificial vagina (not shown) in order to collect the semen flowing therefrom.

The filtration cup 5 is configured in order to remove from the semen entering the collection device 1 an undesirable substance forming a sort of gel called "tapioca", which is found in particular in pigs.

The collection bag 4 is itself configured in order to collect and package the semen once filtered by the cup 5, i.e. the liquid fraction of the semen.

Figure 1:
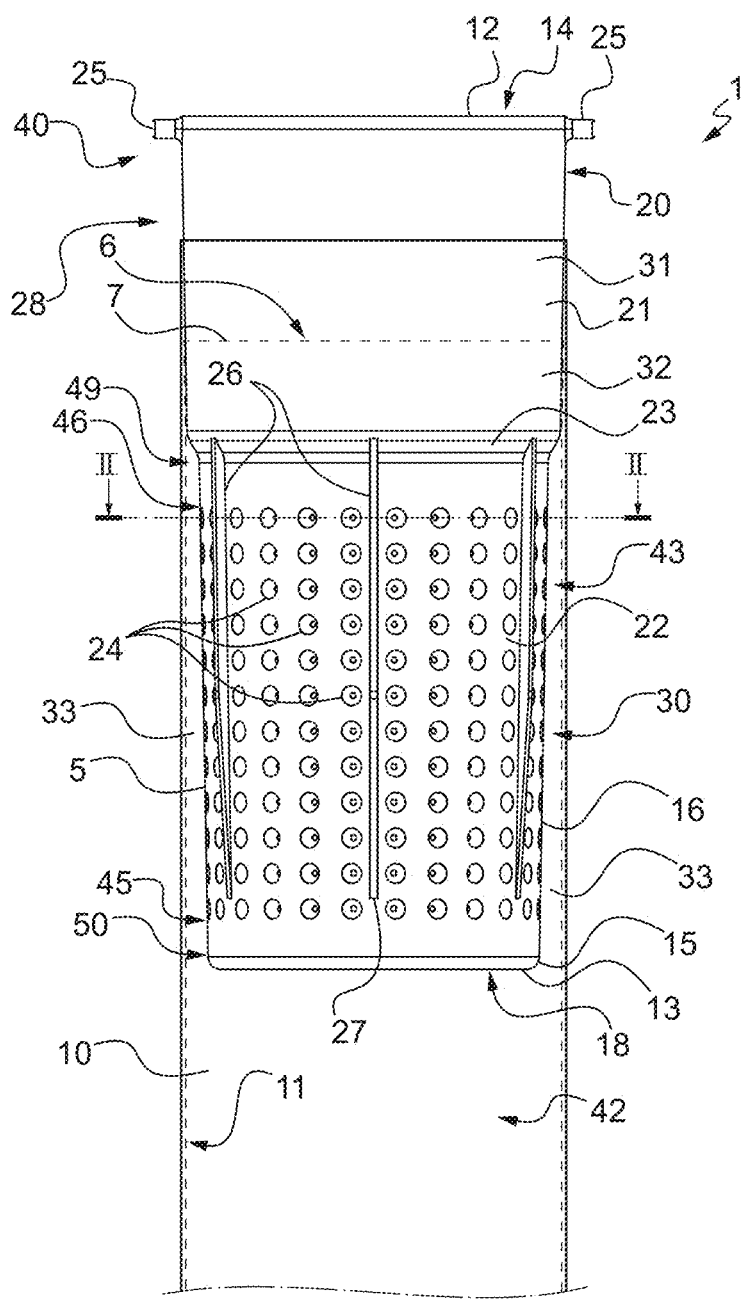
FIG. 1 shows diagrammatically a device for collecting animal semen according to the invention, comprising a filtration cup, a collection bag in which the cup is partially received and a protection bag covering the collection bag.

The collection bag 4 extends longitudinally between a proximal end zone where it has a proximal end 7 turned upwards in FIG. 1, and a distal end zone at which it has a distal end 8 turned downwards in FIG. 1.

At its end 7, the bag 4 has an opening 6, which is thus here turned upwards, while the bottom of the bag 4 is situated at the end 8.

The collection bag 4 is here formed by two films made from thermoplastic material that are extruded and welded edge to edge, except for the edges situated at the end 7 so as to form the opening 6.

The bottom of the bag 4 is thus formed by the welded edges situated at the end 8.

Figure 2:
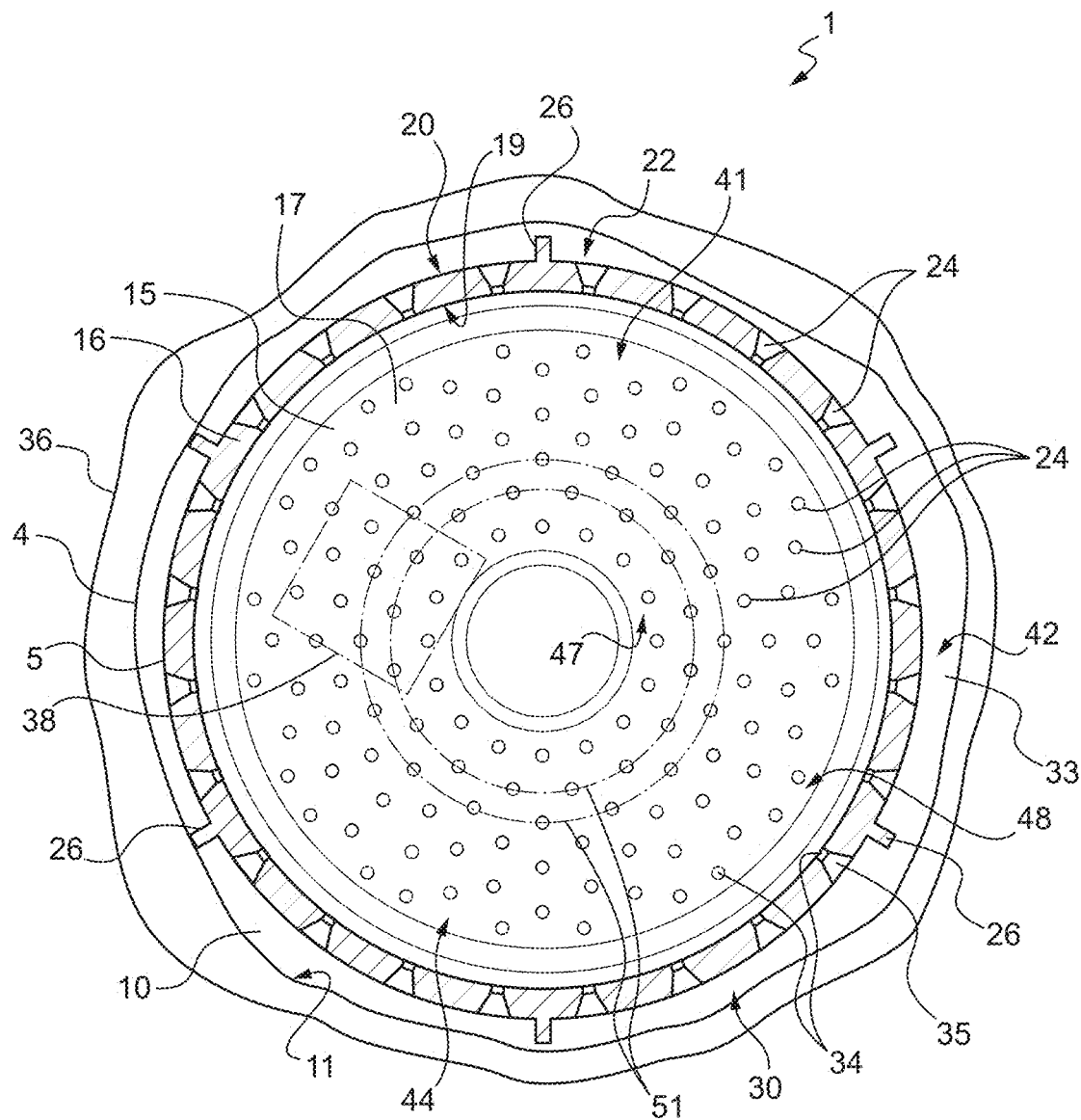
FIG. 2 is the cross-section view referenced II-II in FIG. 1.

In order to simplify the drawings, the welded portions of the films are not shown in FIGS. 1 and 2.

The bag 4 has at rest a generally flattened shape, the films tending to flatten against one another.

When the bag 4 takes up volume, it has a generally tubular shape, visible in cross-section in FIG. 2, with its inner space 10 which is delimited by its inner face 11.

When the bag 4 has taken up volume, it has a transverse cross-section which is here generally circular in shape.

When the bag 4 is held upright, as shown in FIG. 1, the inner face 11 of the bag 4 extends generally vertically between the ends 7 and 8.

Figure 4:
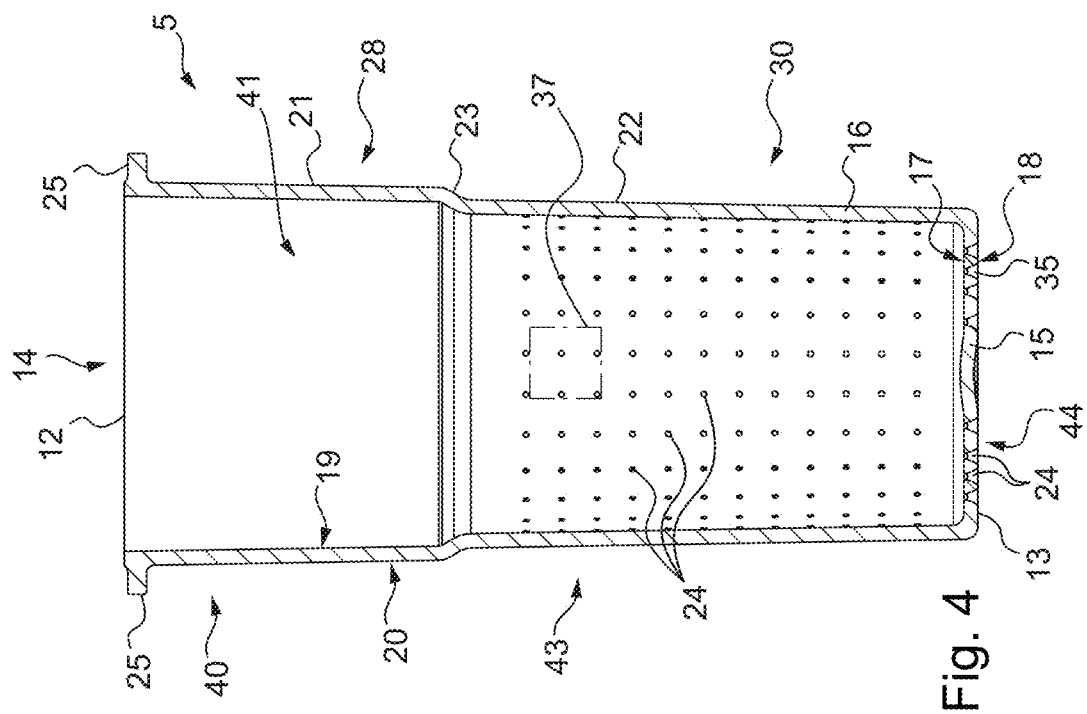
FIG. 4 is a longitudinal cross-section view of the filtration cup.
Figure 3:
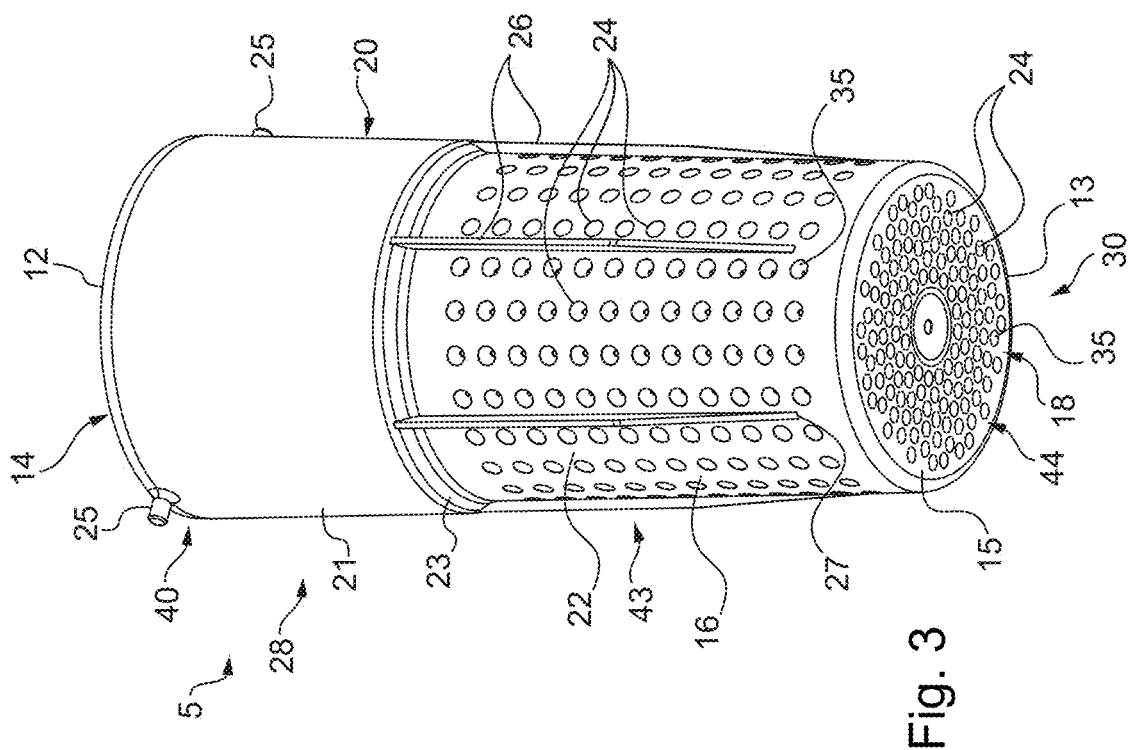
FIG. 3 is a perspective view of the filtration cup taken in isolation, showing in particular the bottom of the cup.

The filtration cup 5 extends longitudinally between an end 12 turned upwards in FIGS. 1, 3 and 4, and an end 13 turned downwards in these same figures.

At its end 12, the cup 5 has an opening 14, which is thus here turned upwards, while the bottom of the cup 5 is situated at the end 13.

The opening 14 forms an inlet opening for the semen in the collection device 1.

The cup 5 is here made from a thermoplastic material comprising a polyolefin-type polymer, here more precisely polypropylene.

The polypropylene is here in a 95% transparent state.

Generally, the material forming the cup 5 is selected so as to be sufficiently translucent or transparent in order to be able to judge the quality of the semen (showing any impurities or traces of blood) and/or to see the fill level of the cup 5 with the semen.

This material is also sufficiently rigid for the cup 5 to be able to maintain a stable predetermined shape in the presence of forces exerted thereon.

The cup 5 is here formed of a single and unique injection-moulded piece. Consequently, all of the parts that comprise the cup 5 form a single piece.

Generally, the cup 5 has an axisymmetric shape.

The cup 5 comprises a bottom wall 15 which extends opposite its opening 14 and a side wall 16 which extends from the bottom wall 15, transversally to the latter, up to the opening 14 that this side wall 16 delimits.

The bottom wall 15 thus forms the bottom of the cup 5.

The thickness of the bottom wall 15 and of the side wall 16 is here approximately 2 mm.

In practice, this thickness can be comprised between 1 mm and 4 mm.

The bottom wall 15 is here flat and extends generally horizontally when the cup 5 is held upright as shown in FIGS. 1, 3 and 4.

It will be noted that the bottom wall 15 has an inner face 17 which delimits the inner space of the cup 5, and an outer face 18 opposite the inner face 17.

The side wall 16 has a generally tubular shape and extends axially in a generally vertical direction when the cup 5 is held upright as shown in FIGS. 1, 3 and 4.

The side wall 16 has a transverse cross-section which is here generally circular in shape.

It will be noted that the side wall 16 has an inner face 19 which delimits the inner space of the cup 5, and an outer face 20 opposite the inner face 19.

The side wall 16 has an upper portion 21, situated towards the opening 14 and delimiting the latter, a lower portion 22 situated towards the bottom wall 15 and connected to the latter, and an intermediate portion 23 connecting the upper portion 21 to the lower portion 22.

Thus, the lower portion 22 extends axially between a first end 49 turned towards the proximal end 7 zone of the bag 4 and connected to the intermediate portion 23, and a second end 50 turned towards the distal end 8 zone of the bag 4 and connected to the bottom wall 15; said bottom wall 15 extends transversally to the lower portion 22 closing the latter (i.e. closing the inner space that it delimits).

It will be noted that in general, the outer diameter of the side wall 16 decreases from the opening 14 up to the bottom wall 15.

The side wall 16 thus has a certain conicity that promotes the stripping of the cup 5 during the manufacture thereof.

It will also be noted that this reduction in diameter is relatively small in the upper portion 21 and in the lower portion 22 so that these portions 21 and 22 are virtually cylindrical in appearance.

Conversely, this reduction in diameter is much more pronounced in the intermediate portion 23 than in the upper 21 and lower 22 portions, so that the outer face 20 has a shoulder at this location.

In general, it will be noted that the outer diameter of the side wall 16 is greater in the upper portion 21 than in the lower portion 22.

Thus, the part of the outer face 20 situated in the lower portion 22 is recessed overall (towards the inside of the cup 5) with respect to the part of the outer face 20 that is situated in the upper portion 21.

The average outer diameter of the upper portion 21 is here approximately 54 mm.

The average outer diameter of the lower portion 22 is here approximately 49 mm.

The difference in average outer diameter between the upper portion 21 and the lower portion 22 is thus here approximately 5 mm.

At the level of the intermediate portion 23 more specifically, the difference in outer diameter between the upper portion 21 and the lower portion 22, i.e. the width of the shoulder, is here approximately 3 mm.

The cup 5 also has a plurality of orifices 24, here arranged both in a region 43 of the lower portion 22 of the side wall 16 and in a region 44 of the bottom wall 15.

These regions thus form respectively a perforated region 43 of the side wall 16 and a perforated region 44 of the bottom wall 15, outside which the side wall 16 and the bottom wall 15 are not perforated by the orifices 24.

The region 43 has a tubular shape and extends between a lower edge 45 turned towards the bottom wall 15 and an upper edge 46 turned towards the upper portion 21.

The region 44 has the shape of a flat ring and extends radially between an inner edge 47 and an outer edge 48.

The orifices 24 are configured in order to allow the semen to escape from the filtration cup 5 while retaining the "tapioca" substance therein.

In particular, the minimum diameter of the orifices 24 is chosen in order to retain the "tapioca" substance.

The lower portion 22 of the side wall 16 and the bottom wall 15 thus together form a perforated wall 30 configured in order to filter the semen, the lower portion 22 forming a tubular portion of the perforated wall 30 while the bottom wall 15 forms a bottom portion of the perforated wall 30.

As shown in particular in FIG. 2, the orifices 24 are each delimited by a surface that here has a cylindrical portion 34, here having a circular cross-section, followed by a funnel-shaped portion 35.

The cylindrical portion 34 is turned towards the inside of the cup 5, while the funnel-shaped portion 35 is turned towards the outside of the cup 5 and increases in diameter towards the outside of the cup 5; i.e. towards the outer face 20 for the orifices 24 arranged in the side wall 16, and towards the outer face 18 for the orifices 24 arranged in the bottom wall 15.

The diameter of the cylindrical portion 34 corresponds to the minimum diameter of the orifice 24, which is here approximately 0.8 mm.

In practice, this minimum diameter can be comprised between 0.5 mm and 1.5 mm.

The diameter of the funnel-shaped portion 35 increases from the minimum diameter up to a maximum diameter which is here approximately 2 mm.

In general, in each of the regions 43 and 44 of the perforated wall 30, the orifices 24 are distributed by being arranged according to a predetermined pattern.

On the side wall 16, and more precisely in the region 43, the orifices 24 are arranged according to a first predetermined pattern having a succession of columns, here twenty-four columns, distributed about the lower portion 22 according to a predetermined angular pitch of approximately 15 degrees.

Each column here comprises twelve orifices 24, the total number of orifices 24 arranged in the lower portion 22 thus being here 24×12=288 orifices.

Each column is orientated longitudinally like the axial orientation of the side wall 16, i.e. here substantially vertically.

Between two adjacent columns, the corresponding orifices 24 are situated at the same height (i.e. these orifices 24 are aligned horizontally) so that, according to this first predetermined pattern, the orifices 24 are also arranged in a grid overall, here more precisely of rectangles (the vertical separation between two adjacent orifices 24 in one and the same column is here less than the horizontal separation between two corresponding orifices 24 in two adjacent columns).

In a variant, between two adjacent columns, the corresponding orifices 24 could be vertically offset so that the orifices 24 would be arranged in a quincunx overall.

On the bottom wall 15, and more precisely in the region 44 which here has the shape of a disk, the orifices 24 are arranged according to a second predetermined pattern having a succession of concentric circles 51, here 8 circles 51 (two of which are represented by a dash-dotted line in FIG. 2).

Each circle 51 here comprises sixteen orifices, with the exception of the outermost circle, which comprises eight additional orifices (i.e. twenty-four orifices in total), the total number of orifices 24 arranged in the bottom wall 15 thus here being 8×16+8=136 orifices.

Between two adjacent circles 51, the corresponding orifices 24 have an angular offset, so that they are not radially aligned and are arranged in a quincunx.

In general, it will be noted that it is possible to characterize the perforated regions 43 and 44 of the perforated wall 30 by a surface density of orifices 24.

For a given perforated region of the perforated wall 30, in which the orifices 24 are arranged according to a given predetermined pattern, the surface density of orifices is here defined by the maximum number of orifices 24 that can be completely enclosed in a square centimetre (1 cm$^2$) of the surface of the perforated wall 30, the surface under consideration here being that of the inner face of the perforated wall 30, i.e. that delimiting the inner space of the cup 5.

This inner face of the perforated wall 30 is here formed by the inner face 17 of the bottom wall 15 and by the part of the inner face 19 of the side wall 16 situated on the lower portion 22 thereof.

In general, i.e. regardless of the perforated region 43 or 44 under consideration, the surface density of orifices 24 on the perforated wall 30 is comprised between 3 and 16 orifices per cm$^2$.

It will be noted that here, in particular, the first predetermined pattern and the second predetermined pattern provide a greater surface density of orifices 24 on the bottom wall 15 than on the side wall 16.

With reference to the perforated region 43, a zone 37 representing 1 cm$^2$ of inner surface of the perforated wall 30 is represented in FIG. 4.

The zone 37 is positioned so as to completely enclose a maximum number of orifices, which here is four orifices 24.

The first predetermined pattern thus provides a surface density of orifices 24 on the lower portion 22 of the side wall 16 which here is 4 orifices per cm$^2$.

In general, the surface density of orifices 24 on the lower portion 22 can be comprised between 3 and 7 orifices per cm$^2$.

With reference to the perforated region 44, a zone 38 representing 1 cm$^2$ of inner surface of the perforated wall 30 is represented in FIG. 2.

The zone 38 is positioned so as to completely enclose a maximum number of orifices 24, which here is twelve orifices 24 (the orifices not completely enclosed in the zone 38 are not counted).

The second predetermined pattern thus provides a surface density of orifices 24 on the bottom wall 15 which here is 12 orifices per cm$^2$.

In general, the surface density of orifices 24 on the bottom wall 15 can be comprised between 10 and 16 orifices per cm$^2$.

It will be noted that here, the first predetermined pattern and the second predetermined pattern provide a uniform surface density of orifices with respect to the whole of the perforated region 43 of the side wall 16 and to the whole of the perforated region 44 of the bottom wall 15.

In a variant, the first and/or second predetermined pattern could provide a surface density of orifices 24 which would be variable according to the positioning of the zone 37 and/or 38 on the respective perforated region 43 and/or 44.

In this case, the surface density of orifices 24 would be defined as being an average surface density of orifices 24 over the whole of the region 43 and/or 44 under consideration, calculated for example by dividing the number of orifices 24 by the area of the inner surface of the perforated wall 30 in the region 43 and/or 44 under consideration.

Here, the outer face of the lower portion 22 is ribbed. More precisely, the cup 5 has a plurality of ribs 26 arranged on the lower portion 22, projecting from the outer face 20.

The ribs 26 here number six and are distributed around the lower portion 22 according to a predetermined angular pitch of approximately 60 degrees.

Each rib 26 is straight and is orientated longitudinally like the axial orientation of the side wall 16, i.e. here substantially vertically.

Each rib 26 emerges from the intermediate portion 23 forming a shoulder and extends in the direction of the bottom wall 15 up to a distal end 27 situated in the vicinity of the bottom wall 15.

At the level of the intermediate portion 23, each rib 26 has a height that is substantially equal to the width of the shoulder, then retains a constant height from the intermediate portion 23 up to approximately midway along the length, then decreases in height up to its distal end 27 where the rib 26 is then flush with the outer face 20.

It will be noted here that by means of the rigid nature of the material forming the cup 5, it is possible to arrange the ribs 26 on the perforated wall 30 itself, whereas this would not have been possible with a non-woven fabric filter.

The cup 5 also has two locking pins 25, projecting on either side of the upper portion 21 and here situated in the vicinity of the opening 14.

These locking pins 25 form with the part of the upper portion 21 that bears them a mechanical connection interface 40 for connecting the collection device 1 to the artificial vagina.

More generally, the upper portion 21 and the locking pins 25 form an inlet element 52 of the collection device 1, comprising the mechanical connection interface 40 and delimiting the opening 14.

It will be noted that the perforated wall 30 forms a filter associated with this inlet element 52 and delimiting with the inlet element 52 an inlet chamber 41 (FIG. 4) for the inlet of the semen into the collection device 1; said inlet chamber 41 extends on the side of a first face of the filter turned towards the opening 14.

The inlet chamber 41 here corresponds to the inner space of the cup 5, while the first face of the filter here corresponds to the inner face of the perforated wall 30.

As shown in FIGS. 1 and 2, the cup 5 is partially received in the bag 4, through the opening 6 thereof, to a depth such that the lower portion 22 is entirely received in the bag 4.

In particular, the perforated wall 30 is entirely received in the bag 4.

It will be noted that the perforated wall 30 delimits with the bag 4 a collection chamber 42 for the filtered semen; said collection chamber 42 extends on the side of a second face of the filter (which is formed by the perforated wall 30) turned towards the distal end 8 zone of the bag 4.

The second face of the filter here corresponds to the outer face of the perforated wall 30, i.e. the face here formed by the outer face 18 of the bottom wall 15 and by the part of the outer face 20 of the side wall 16 situated on the lower portion 22 thereof.

The upper portion 21 is itself engaged in the proximal end 7 zone of the bag 4, in particular in the opening 6 so as to hold the bag 4 open.

It will be noted that the average outer diameter of the upper portion 21 corresponds substantially to the inner diameter of the bag 4.

It will also be noted that since the part of the outer face 20 situated in the lower portion 22 is recessed overall (towards the inside of the cup 5) with respect to the part of the outer face 20 that is situated in the upper portion 21, the collection chamber 42 has a space 33 extending between the part of the outer face 20 situated in the lower portion 22 and the inner face 11 of the bag 4.

The upper portion 21 here has an outer part 31 which projects outwardly beyond the end 7 of the bag 4 and an inner part 32 received in the bag 4.

The locking pins 25 are borne by the outer part 31.

At the level of the inner part 32, the inner face 11 of the bag 4 is fixed to the outer face 20 of the side wall 16, i.e. on the outer perimeter of the inlet element 52, here by heat welding.

It will be noted that the thermoplastic material of the films forming the bag 4 here comprise a polyolefin-type polymer, which has been selected in order to be chemically miscible with the polypropylene forming the cup 5.

The collection device 1 here also comprises a protection bag 36, similar to the collection bag 4 and covering the latter in order to protect it from possible soiling, in particular from bacterial contamination.

The collection bag 4 here is entirely received in the protection bag 36.

The bag 36 is fixed to the upper portion 21 of the cup 5 in the same manner as the collection bag 4, the welding between the bag 36 and the upper portion 21 being carried out between the end 7 of the collection bag 4 and the end 12 of the cup 5.

It will be noted that the material forming the bags 4 and 36 is chosen so as to be sufficiently translucent or transparent in order to be able to judge the quality of the semen (showing any impurities or traces of blood) and/or to see the fill level of the cup 5 or of the bag 4 with the semen.

In order to collect the semen, the collection device 1 is connected to the outlet of the artificial vagina by means of the connection interface 40 of the cup 5.

The artificial vagina is mounted on the penis of an animal and actuated in order to stimulate it.

The semen leaving the artificial vagina enters via the opening 14 and flows into the inlet chamber 41, which it fills partially, then passes through the perforated wall 30 and is collected in the collection chamber 42.

The volume of semen produced by the animal (the ejaculate) is thus progressively filtered by the perforated wall 30.

During the filtration, the "tapioca" substance tends to accumulate at the bottom of the cup 5 and to block the orifices 24 in the bottom wall 15, so that after a certain moment, the semen, and more accurately the liquid fraction thereof, has difficulty flowing through the orifices 24 in the bottom wall 15. The orifices 24 in the side wall 16 allow the liquid fraction of the semen to continue to flow through the perforated wall 30 under optimum conditions.

The semen filtered by the side wall 16 thus flows into the space 33 before falling to the bottom of the bag 4.

It will be noted that by means of the space 33, the risk is reduced of the films of the bag 4 flattening against the perforated wall 30 and plugging the orifices 24.

The ribs 26, which project into the space 33, make it possible to further reduce this risk by holding the films of the bag 4 away from the outer face 20 even when these films have a tendency to get close to one another, for example if the cup 5 is tilted.

By means of the space 33 and the ribs 26, it is thus possible to confer a virtually cylindrical shape on the perforated wall 30 without risking plugging the orifices 24 in the perforated wall 30.

Compared with a conical shape, this cylindrical shape offers a greater surface area in order to arrange the orifices 24 in the side wall 16 and in the bottom wall 15 of the cup 5; it is thus possible for there to be a greater number of orifices 24 than on a similar, but conical, wall.

The cylindrical shape also makes it possible for the volume delimited by the perforated wall 30 to be larger than if the latter were conical. In this way, a greater quantity of "tapioca" can be received in the cup 5 while retaining a sufficient number of non-blocked orifices 24 on the side wall 16 in order to allow the liquid fraction to flow.

Moreover, the applicant has observed that, under certain conditions, such a perforated wall 30 makes it possible to provide exceptional performance with regard to the semen filtration speed, in comparison with the non-woven textile filtration pouch of the collection device described in the international application WO 2006/131781.

For example, during tests carried out with semen from boars of the Piétrain breed, the applicant has observed that for a given volume of semen to be filtered resulting in a volume of collected filtered semen comprised between 300 and 400 ml, while the filtration time is comprised between 2 and 4 minutes when using a collection device having a filtration pouch of non-woven fabric, this filtration time is comprised between 15 and 60 seconds when using the collection device 1 equipped with the perforated wall 30.

In addition, the volume of the liquid fraction of the semen retained by dampening (and thus not collected in the bag 4) is much less when this semen is filtered with the perforated wall 30 than when it is filtered with the pouch of non-woven fabric.

The tests carried out by the applicant have in fact shown that, for a given volume of semen to be filtered, while between 7% and 8% of the liquid fraction of this volume (i.e. the part of the volume of semen without the "tapioca" substance) is retained by dampening on the pouch of non-woven fabric, less than 1% of the liquid fraction of this volume is retained by the perforated wall 30.

In addition, the concentration and the motility of the spermatozoids are not impaired by the perforated wall 30 and are in fact similar to those observed when the semen is filtered by the filtration pouch of non-woven fabric.

It will also be noted that the polypropylene forming the cup 5 has a relatively low surface tension, here approximately 29 dynes, which confers hydrophobic properties on the surface of the perforated wall 30 and promotes the flow of the semen through the orifices 24.

In practice, the material from which the cup 5 is made can be chosen so as to have a surface tension less than 30 dynes.

Once the collection operation is finished, the bag 36 is removed and the portion of the bag 4 in which the filtered semen is received can then be separated from the rest of the device 1, for example by tearing the films, and taken to a laboratory for analysis and packaging, where the semen is analyzed and diluted before being preserved in individual packets.

In order to facilitate the tearing of the films, the collection 4 and/or protection 36 bag can each be provided with a notch (not shown), arranged in the welded portions of the films so as to form a pre-cutout therein.

In a variant, the bags 4 and/or 36 are opaque to light, or to certain specific wavelengths of electromagnetic radiation that are harmful to the preservation of the semen, for example UV and/or IR rays.

To this end, pigments for protecting against such rays can be introduced into the material from which the bags 4 and 36 are made and/or can be printed on the surface of this material.

In other variants that are not shown:
the thermoplastic material from which the cup is made is devoid of polypropylene and comprises another material, for example polyethylene;
the thermoplastic material from which the cup is made is not a polyolefin-type polymer but another type, for example polyacetal-type;
the material from which the cup is made is not a thermoplastic but of a different type, for example metallic, such as stainless steel, the cup then being produced by stamping and piercing;
the welding between the bag and the cup is not thermal but is carried out differently, for example by ultrasound, or by laser, with one of the materials of the cup and of the bag being transparent to the laser wavelength while the other of the materials is made to be opaque to this wavelength, for example using pigments that absorb this wavelength incorporated into this other material;
the bag and the cup are not welded but rather are fixed by bonding, or using an elastic ring gripping the bag onto the cup;
the side wall of the cup has an elliptical, rectangular or square cross-section, rather than circular;
the bottom wall of the cup is not flat but for example incurved or conical;
the first predetermined pattern comprises more or less than twenty-four columns of orifices; these orifices are arranged differently than in a grid of rectangles, for example in a grid of squares, or are arranged in a quincunx;

according to the second predetermined pattern, the orifices are arranged differently than in a quincunx, for example in a grid of rectangles or squares;

the cylindrical portion of the orifices is turned towards the outside of the cup, while the funnel-shaped portion is turned towards the inside of the cup and broadens towards the inside of the cup;

the orifices are devoid of a funnel-shaped portion and are only cylindrical, or conversely are devoid of a cylindrical portion and are only funnel-shaped;

the cup is devoid of an intermediate portion forming a shoulder;

the cup has more, or less, than six ribs on its lower portion, the predetermined angular pitch according to which the ribs are distributed being adapted as a result;

the ribs are configured differently, and are for example annular and orientated in a plane perpendicular to the direction of longitudinal extension of the tubular side wall;

the ribs are not continuous but interrupted and/or have a constant height over their entire length;

the connection interface is devoid of locking pins and instead comprises for example a screw thread for screwing the cup into the outlet neck of the artificial vagina; and/or the collection device is devoid of a protection bag.

Numerous other variants are possible depending on circumstances and it is recalled in this regard that the invention is not limited to the examples described and shown.

The invention claimed is:

1. A collection device for the collection of animal semen, comprising:

an inlet element comprising a mechanical interface connector configured to connect to an artificial vagina and delimiting an inlet opening in the collection device;

a filter formed by a perforated wall comprising a first face and a second face, said perforated wall associated with the inlet element, said first face delimiting with the inlet element an inlet chamber; and a collection bag extending between a closed distal end zone and a proximal end zone, said proximal end zone having an opening in-which is fixed to said inlet element; said collection bag and said second face of said filter delimiting a collection chamber;

wherein semen entering the collection device via the inlet opening passes through the filter and is collected in the collection chamber; and wherein the perforated wall has a tubular portion extending axially between a first end closest to said proximal end zone of said collection bag and a second end closest to said closed distal end zone of said collection bag and a bottom portion extending transversally to said tubular portion and closing the second end of the tubular portion; said perforated wall is perforated by a plurality of orifices distributed over said tubular portion according to a first predetermined pattern and on said bottom portion according to a second predetermined pattern, said first predetermined pattern and second predetermined pattern providing a surface density of orifices that is greater on said bottom portion than on said tubular portion.

2. The collection device according to claim 1, characterized in that said tubular portion has a circular cross-section.

3. The collection device according to claim 1, characterized in that said second face of said tubular portion is a ribbed outer face.

4. The collection device according to claim 3, characterized in that said ribbed outer face has straight ribs longitudinally oriented along the tubular portion.

5. The collection device according to claim 4, characterized in that said ribs are distributed around the tubular portion, according to a predetermined angular pitch.

6. The collection device according to claim 1, characterized in that said plurality of orifices have a predetermined minimum diameter between 0.5 mm and 1.5 mm, said surface density of orifices being between 3 and 16 orifices per $cm^2$.

7. The collection device according to claim 1, characterized in that said first predetermined pattern provides a surface density of orifices on the tubular portion between 3 and 7 orifices per $cm^2$.

8. The collection device according to claim 1, characterized in that said second predetermined pattern provides a surface density of orifices on the bottom portion between 10 and 16 orifices per $cm^2$.

9. The collection device according to claim 1, characterized in that, according to at least one of said first predetermined pattern and said second predetermined pattern, said plurality of orifices are arranged in a grid of rectangles.

10. The collection device according to claim 1, characterized in that, according to at least one of said first predetermined pattern and said second predetermined pattern, said plurality of orifices are arranged in a quincunx.

11. The collection device according to claim 1, characterized in that each of said plurality of orifices is delimited by a funnel-shaped surface increasing in diameter towards the second face of the filter.

12. The collection device according to claim 1, characterized in that said inlet element and said perforated wall are formed of injection-moulded thermoplastic material.

13. The collection device according to claim 1, characterized in that the material from which said perforated wall is made comprises a polyolefin-type polymer having a surface tension less than 30 dynes.

14. The collection device according to claim 1, further comprising a protection bag which covers said collection bag and which is fixed to said inlet element.

* * * * *